US010709405B2

(12) United States Patent
Ahn

(10) Patent No.: US 10,709,405 B2
(45) Date of Patent: Jul. 14, 2020

(54) X-RAY CT SCANNING APPARATUS AND SCANNING METHOD THEREOF

(71) Applicants: VATECH Co., Ltd., Gyeonggi-do (KR); VATECH EWOO Holdings Co., Ltd., Gyeonggi-do (KR)

(72) Inventor: Byung-Jun Ahn, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 180 days.

(21) Appl. No.: 15/771,390

(22) PCT Filed: Oct. 26, 2016

(86) PCT No.: PCT/KR2016/012044
§ 371 (c)(1),
(2) Date: Apr. 26, 2018

(87) PCT Pub. No.: WO2017/073996
PCT Pub. Date: May 4, 2017

(65) Prior Publication Data
US 2018/0333127 A1    Nov. 22, 2018

(30) Foreign Application Priority Data

Oct. 26, 2015  (KR) .................. 10-2015-0148910

(51) Int. Cl.
*A61B 6/06*  (2006.01)
*A61B 6/00*  (2006.01)
(Continued)

(52) U.S. Cl.
CPC .............. *A61B 6/542* (2013.01); *A61B 6/032* (2013.01); *A61B 6/06* (2013.01); *A61B 6/14* (2013.01);
(Continued)

(58) Field of Classification Search
CPC .... A61B 6/00; A61B 6/03; A61B 6/06; A61B 6/542; A61B 6/032; A61B 6/14;
(Continued)

(56) References Cited

U.S. PATENT DOCUMENTS

2004/0013225 A1   1/2004  Gregerson et al.
2005/0254621 A1   11/2005  Kalender et al.
(Continued)

FOREIGN PATENT DOCUMENTS

KR    10-2009-0053768 A    5/2009
KR    10-2009-0130719 A    12/2009
(Continued)

OTHER PUBLICATIONS

Korean Intellectual Property Office, International Search Report of International Application No. PCT/KR2016/012044, dated Feb. 14, 2017.
(Continued)

*Primary Examiner* — Jurie Yun
(74) *Attorney, Agent, or Firm* — IP Legal Services, LLC

(57) ABSTRACT

Disclosed is an X-ray CT radiographing apparatus capable of selecting various FOVs, simplifying radiographing motion, and reducing X-ray exposure dose, and a method thereof. An X-ray CT radiographing apparatus according to the present invention includes a rotation supporter rotating by a rotation driver, a generating unit including an X-ray generator emitting X-rays and a collimator so as to radiate a collimated X-ray beam, a sensing unit including a small width X-ray sensor moving in a tangential direction of a rotation trajectory, and a controller controlling operations of the rotation driver, the generating unit, and the sensing unit when performing X-ray radiographing, and configuring movement trajectories of an X-ray beam for radiographing FOVs different from each other to be the same, and con-
(Continued)

trolling the generating unit to turn OFF the X-ray beam in sections different from each other of the movement trajectory of the X-ray beam according to the FOV.

8 Claims, 5 Drawing Sheets

(51) Int. Cl.
  *A61B 6/14* (2006.01)
  *A61B 6/03* (2006.01)
  *G06T 11/00* (2006.01)
(52) U.S. Cl.
  CPC ............ *A61B 6/405* (2013.01); *A61B 6/4435* (2013.01); *A61B 6/4452* (2013.01); *G06T 11/003* (2013.01); *G06T 2211/436* (2013.01)
(58) Field of Classification Search
  CPC ........... A61B 6/035; A61B 6/10; A61B 6/107; A61B 6/44; G06T 11/00; G06T 11/003; G06T 2211/436; G06T 2211/40; G01N 23/046; H05G 1/56; G21K 1/02
  USPC ..... 378/4, 11, 16, 19, 38, 39, 114, 116, 117, 378/147, 151, 160
  See application file for complete search history.

(56) References Cited

U.S. PATENT DOCUMENTS

| | | |
|---|---|---|
| 2007/0086566 A1 | 4/2007 | Gregerson et al. |
| 2007/0242794 A1 | 10/2007 | Stanton et al. |
| 2007/0242797 A1 | 10/2007 | Stewart et al. |
| 2007/0242868 A1 | 10/2007 | Stanton et al. |
| 2009/0262893 A1 | 10/2009 | Stewart et al. |
| 2009/0274272 A1 | 11/2009 | Stanton et al. |
| 2010/0142671 A1 | 6/2010 | Gregerson et al. |
| 2011/0012897 A1 | 1/2011 | Stanton et al. |
| 2012/0219202 A1 | 8/2012 | Stanton et al. |
| 2012/0243762 A1 | 9/2012 | Kanerva et al. |
| 2013/0170610 A1 | 7/2013 | Arai et al. |
| 2014/0140470 A1* | 5/2014 | Cho ..................... A61B 6/405 378/19 |
| 2014/0205074 A1 | 7/2014 | Gregerson et al. |
| 2015/0206614 A1 | 7/2015 | Roh et al. |
| 2015/0230766 A1 | 8/2015 | Wang et al. |
| 2016/0213336 A1 | 7/2016 | Kim et al. |
| 2016/0331335 A1 | 11/2016 | Gregerson et al. |

FOREIGN PATENT DOCUMENTS

| | | |
|---|---|---|
| KR | 10-2010-0115000 A | 10/2010 |
| KR | 10-2012-0107438 A | 10/2012 |
| KR | 10-2013-0003259 A | 1/2013 |
| KR | 10-1384601 B1 | 4/2014 |
| KR | 10-2015-0024706 A | 3/2015 |
| KR | 10-2015-0062521 A | 6/2015 |
| KR | 10-2015-0086693 A | 7/2015 |
| WO | 2014/047518 A1 | 3/2014 |

OTHER PUBLICATIONS

Korean Intellectual Property Office, Written Opinion of International Application No. PCT/KR2016/012044, dated Feb. 14, 2017.
European Patent Office, European Search Report of corresponding EP Patent Application No. 16860179.7, dated Jun. 11, 2019.

* cited by examiner

X-RAY CT SCANNING APPARATUS AND SCANNING METHOD THEREOF

CROSS REFERENCE TO RELATED APPLICATIONS

This application is a National Stage Patent Application of PCT International Patent Application No. PCT/KR2016/012044 (filed on Oct. 26, 2016) under 35 U.S.C. § 371, which claims priority to Korean Patent Application No. 10-2015-0148910 (filed on Oct. 26, 2015), the teachings of which are incorporated herein in their entireties by reference.

TECHNICAL FIELD

The present invention relates to an X-ray CT radiographing apparatus and a radiographing method thereof. More particularly, the present invention relates to an X-ray CT radiographing apparatus capable of providing a three-dimensional X-ray image for a field of view (FOV) having a desired size and shape by using a sensor with a small width and using a low dose of X-rays, and a radiographing method thereof.

BACKGROUND ART

In the medical field, an X-ray radiographing apparatus refers to an apparatus that radiates a predetermined amount X-rays toward a body part to be radiographed, senses the X-rays having passed therethrough by using an X-ray sensor, and reconstructs an X-ray image by using electrical signals sensed by the X-ray sensor. The X-rays having passed through the body part are attenuated in a rate varying according to substances in their travelling path and are transformed to electrical signals by the X-ray sensor by photoelectric. The X-ray radiographing apparatus provides information of interior of the radiographing target in an X-ray image by using electrical signals in which accumulated attenuation rate is reflected according to the X-ray travelling path.

In the field of dental diagnosing, CT images are widely used as the CT images accurately and clearly display a three-dimensional X-ray image of the teeth arrangement, temporomandibular joint or head of the patient, which are main parts of interest among body parts, and tomographic images according to the position and direction desired by the user. Accordingly, such images are used in fields requiring high precision such as implant treatment. An X-ray computed tomography (CT) radiographing apparatus reconstructs X-ray images of a radiographing target which are radiographed in various angles, and provides a three-dimensional X-ray image of the radiographing target. For this, the X-ray CT radiographing apparatus includes an X-ray generator, an X-ray sensor disposed to face the X-ray generator with a subject disposed therebetween, a rotation supporter rotating the X-ray generator and the X-ray sensor while supporting the same, and an image reconstructing unit implementing a CT image by using results sensed by the X-ray sensor.

In order to obtain an X-ray CT image, the X-ray generator and the X-ray sensor rotates facing each other within a predetermined angular range based on a rotation shaft passing through the radiographing target, and X-ray CT data of a field of view in various angles, that is a FOV, is obtained. When performing general X-ray CT radiographing, the X-ray generator and the X-ray sensor rotates around the central axis of the FOV as a rotating axis, and X-rays having passed the entire area of the FOV are received in various angles. Accordingly, for panoramic X-ray image radiographing, a large-size sensor is significantly larger than the X-ray sensor is required.

In one embodiment, describing a case of obtaining an X-ray CT image of a FOV having a first height t1 and a first width w1 by using an X-ray having a cone beam form which is widely used in the dental field, a second height t2 of a sensor has to be equal to or greater than magnification ratio*first height t1, the magnification ratio is defined as the ratio of the distance between the X-ray generator and the examinee to the distance between the X-ray generator and the X-ray sensor (t2≥magnification ratio*t1), and a second width w2 of the sensor has to be equal to or greater than magnification ratio*first width w1 (w2≥magnification ratio*w1) so that the sensor may receive X-rays having passed all areas of the FOV. Herein, if necessary, a method of using a half beam which downsizes the second width of the sensor up to maximum magnification ratio*(w1)/2 by using an X-ray beam covering ½ or more of the FOV. However, when using a half beam method in a conventional X-ray CT radiographing apparatus, a relatively large-size X-ray sensor is required. In addition, there is a problem that a relatively large amount of X-ray exposure is required.

DISCLOSURE

Technical Problem

Accordingly, the present invention has been made keeping in mind the above problems occurring in the prior art, and an object of the present invention is to provide an X-ray CT radiographing apparatus capable of providing an X-ray CT image of a FOV having a desired size and shape by using a sensor with a width narrower than a conventional X-ray CT radiographing apparatus using a half beam method, and using a low dose of X-rays, and a radiographing method thereof.

In addition, another object of the present invention is to provide an X-ray CT radiographing apparatus capable of expanding or selecting a FOV in a free shape without additionally moving or configuring a rotation shaft of a rotation supporter which rotates an X-ray generator and an X-ray sensor facing to each other, of simplifying motion of a radiographing unit when performing an X-ray CT radiographing sequence, and of reducing X-ray exposure amount according to a size or shape of the FOV, and a radiographing method thereof.

Technical Solution

In order to accomplish the above object, an X-ray CT radiographing apparatus according to one aspect of the present invention includes: a rotation supporter rotating by a rotation driver; a generating unit disposed in a first side of the rotation supporter, and including an X-ray generator emitting X-rays and a collimator to radiate a collimated X-ray beam; a sensing unit disposed in a second side of the rotation supporter to face the generating unit with a FOV in between, and including a small width X-ray sensor moving in a tangential direction of a rotation trajectory when the rotation supporter rotates; and a controller substantially blocking the X-rays radiated toward the FOV in at least several sections when performing X-ray radiographing.

An X-ray CT radiographing apparatus according to another aspect of the present invention includes: a rotation supporter rotating by a rotation driver; a generating unit disposed in a first side of the rotation supporter, and including an X-ray generator emitting X-rays and a collimator to radiate a collimated X-ray beam; a sensing unit disposed in a second side of the rotation supporter to face the generating unit with a FOV in between, and including a small width X-ray sensor moving in a tangential direction of a rotation trajectory when the rotation supporter rotates; and a controller controlling operations of the rotation driver, the generating unit, and the sensing unit when performing X-ray CT, wherein the controller selectively substantially blocks the X-ray beam radiated toward the FOV in several sections of a movement trajectory of the X-ray beam radiated toward the FOV according to the FOV.

In the above, the controller may stop the emission of the X-rays from the X-ray generator for the several sections The controller may physically block the X-rays emitted from the X-ray generator for the several sections by using the collimator.

The generating unit may further include a shutter physically blocking the X-ray beam emitted from the X-ray generator for the several sections.

The apparatus may further include an image reconstructing unit providing a three-dimensional X-ray image for at least one part within the FOV by reconstructing a detection result of the X-ray sensor.

An X-ray CT radiographing method according to another aspect of the present invention includes: receiving an input of a position and a shape of a FOV; and performing X-ray radiographing for the FOV by rotating a generating unit including an X-ray generator and, in association thereof, simultaneously rotating a sensing unit including an X-ray sensor with the FOV in between, the X-ray sensor moving in a tangential direction of the rotation trajectory, and substantially blocking X-rays emitted from the X-ray generator toward the FOV in at least several sections according to the position and the shape of the FOV when performing X-ray radiographing.

In the X-ray radiographing, the X-rays may be substantially blocked by controlling the X-ray generator to be turned ON/OFF or by physically blocking the X-ray beam radiated toward the FOV.

After the X-ray radiographing, the method may further include providing a three-dimensional X-ray image for at least one part within the FOV by reconstructing a result detected by the X-ray sensor Advantageous Effects According to the present invention, the present invention, there can be provided an X-ray CT image of a FOV with various sizes and shapes by using a sensor with a width narrower than a conventional X-ray CT radiographing apparatus using a half beam method while using a low dose of X-rays.

In addition, according to the present invention, since a FOV can be expanded or selected in a free shape without additionally moving or configuring a rotation shaft of a rotation supporter which rotates an X-ray generator and an X-ray sensor facing each other, motion of a radiographing unit can be simplified when performing an X-ray CT radiographing sequence in spite of the various types of FOVs that may be radiographed. In addition, by minimizing the amount of X-ray exposure in parts other than the FOV, as a result the X-ray exposure dose of an examinee can be reduced.

MODE FOR INVENTION

Figure 1:
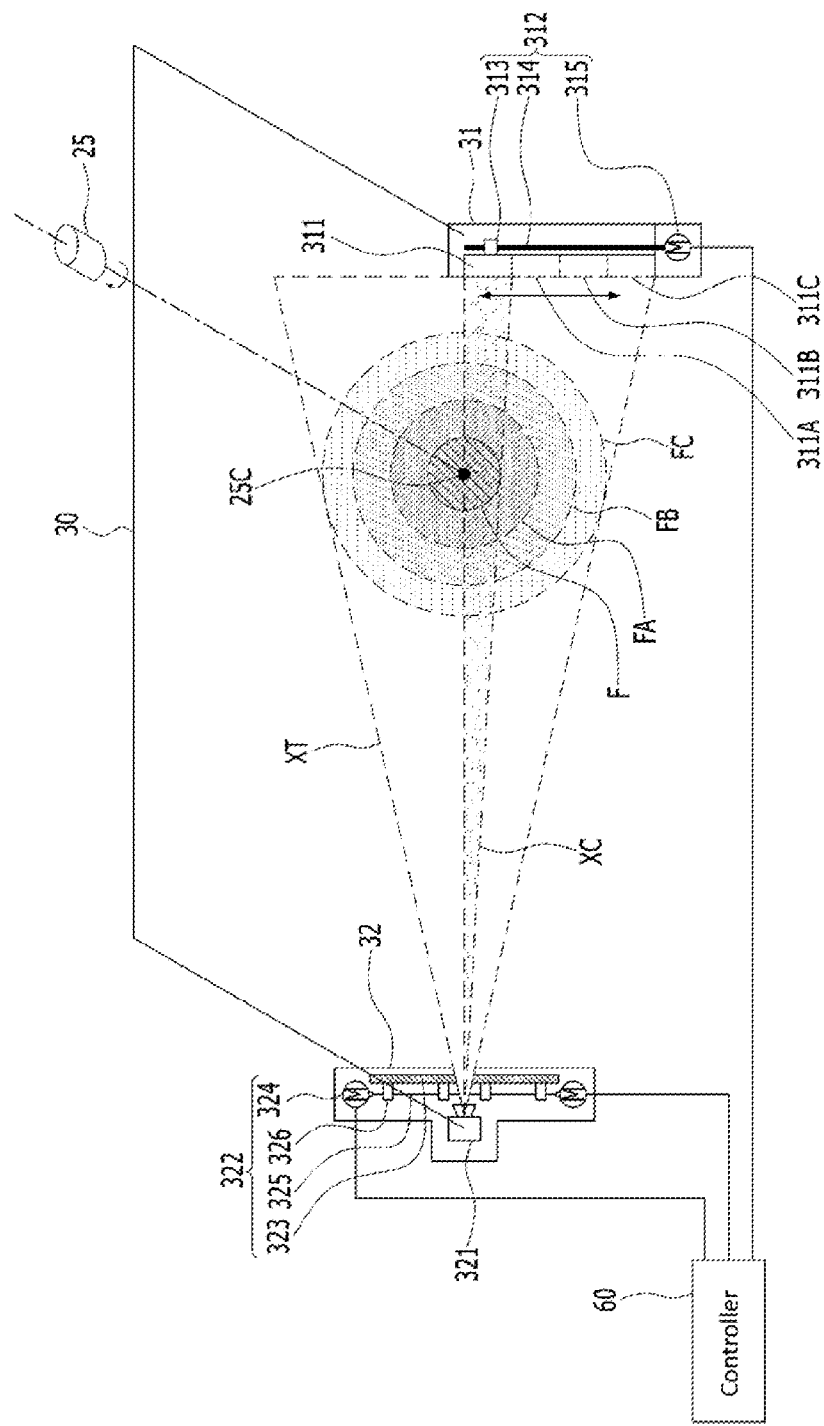
FIG. 1 is a view showing a configuration of a X-ray CT radiographing apparatus and an expansion of a FOV according to a movement of a small width X-ray sensor according to an embodiment of the present invention.

Hereinbelow, exemplary embodiments of the present invention will be described in detail with reference to the accompanying drawings. The embodiments set forth herein are provided for illustrative purposes to fully convey the concept of the present invention. It will be apparent to a person skilled in the art that the present invention should not be construed to be limited to these embodiments. Throughout the drawings, the same reference numerals will refer to the same or like parts. Descriptions of some components depicted in a specific drawing will be omitted, when their reference numerals are identical to those of the components described with reference to another drawing.

FIG. 1 is a view showing a configuration of an X-ray CT radiographing apparatus and an expansion of a FOV according to a movement of a small width X-ray sensor according to an embodiment of the present invention The present figure schematically shows a configuration of a radiographing unit of an X-ray CT radiographing apparatus, wherein the radiographing unit performs an X-ray CT radiographing sequence by receiving a control signal from a controller 60. When performing the X-ray CT radiographing sequence, a radiation path of an X-ray beam partially passing through a subject is rotated, at the same time, a virtual X-ray beam center is moved so that the X-ray beam is irradiated on all parts within a FOV in various angles and in a predetermined range or more. In order to implement the same, the radiographing unit includes a rotation driver 25, a rotation supporter 30 rotating based on a rotation shaft 25C by the rotation driver 25, a generating unit 32 disposed in a first side of the rotation supporter 30 and including an X-ray generator 321 and a collimator 322 so as to generate an X-ray beam collimated in a predetermined width, and a sensing unit 31 disposed in a second side of the rotation supporter 30 to face the generating unit 32 with the subject in between and including a small width X-ray sensor 311 moving in a direction to where the rotation supporter 30 rotates.

The sensing unit 31 includes the small width X-ray sensor 311 facing the generating unit 32. Herein, when the total height and width of a FOV of a CT image to be obtained are respectively t1 and w1 (herein, height refers to a maximum size in a direction parallel to a rotation shaft, width refers to a maximum size in a direction perpendicular to the rotation shaft), a height t2 of the small width X-ray sensor is equal to or greater than magnification ratio*first height (t1) (t2≥magnification ratio*t1), and a width w2 of the small width X-ray sensor is less than magnification ratio*first width w1/2 (w2<magnification ratio*w1/2). In addition the small width X-ray sensor 311 is installed to move in a rotation trajectory of the sensing unit 31 based on the rotation shaft 25C, for example, in a tangential direction of a circular trajectory, and the generating unit 32 emits an X-ray beam XC toward the small width X-ray sensor 311 in association with the movement of the small width X-ray sensor 311.

In the present figure, concentric circles F, FA, FB, and FC based on the rotation shaft 25C are FOVs expanded according to a movement range of the small width X-ray sensor 311. For example, when the small width X-ray sensor 311 is in a fixed state at an initial position represented in a solid line and the rotation supporter 30 rotates at a predetermined angle or more, for example 360 degrees, an X-ray CT image of the smallest FOV F may be obtained. The above case is substantially identical to a conventional half beam X-ray CT radiographing apparatus. In addition, during continuous X-ray image radiographing accompanied with additional rotations based on the rotation shaft 25C, when the small width X-ray sensor 311 moves from the position represented in a solid line by, for example, a width thereof in a tangential direction, that is to 311A, a FOV FA expands in radius by the width of the small width X-ray sensor 311. Similarly, during continuous radiographing, when the small width X-ray sensor 311 moves by twice of the width thereof, or when the small width X-ray sensor 311 moves by three times of the width thereof, FOVs FB and FC also expand in response to the increase in a movement range. Accordingly, the width of the small width X-ray sensor 311 is smaller than a value obtained by multiplying radius of actual expanded FOVs FA, FB, and FC by a maximum magnification ratio.

In reference, for a convenience of description, in the above description, movements of the small width X-ray sensor 311 are performed in stages according to a rotation period based on the rotation shaft 25C. Preferably, the movements of the small width X-ray sensor 311 may be performed while the rotation based on the rotation shaft 25C is performed. Description thereof will be easily understood by a description below with reference to FIG. 2.

In terms of apparatus configuration, the sensing unit 31 includes a small width X-ray sensor driver 312 moving the small width X-ray sensor 311 in a tangential direction of a rotation trajectory within a limited range. The small width X-ray sensor driver 312 may be configured to have, for example, a motor 315 generating driving power, a driving shaft 314 transferring the generated driving power, and a connector 313 connecting a part of the small width X-ray sensor 311 and the driving shaft 314. However, such a mechanical configuration is merely an example and may be implemented in various forms.

Meanwhile, the generating unit 32 radiates an X-ray beam XC with a width sufficient to cover the width of the small width X-ray sensor 311 focused in association with the positional movement of the small width X-ray sensor 311. As a configuration example for the same, the generating unit 32 may include an X-ray generator 321 emitting an X-ray beam XT with a wide width covering the movement range of the small width X-ray sensor, and a collimator 322 adjusting the X-ray beam XT with the wide width, and emitting an X-ray beam XC with a narrow width covering the width of the small width X-ray sensor 311 and focused according to the position of the small width X-ray sensor 311. The collimator 322 may be configured to have at least one blade 323 capable of partially shielding an X-ray beam, a motor 324 generating, for example, driving power for moving the at least one blade 323, a driving shaft 325 transferring the generated driving power, and a connector 326 connecting a part of the 323 and the driving shaft 325. The collimator 322 may drive one blade having a slit with a predetermined width and which passes through the focused X-ray beam XC by using one motor, or may drive at least two blades by using a motor separately provided.

However, such a configuration of the above-mentioned generating unit 32 is merely an example, and may be implemented in various forms. For example, the generating unit 32 may be configured to have an X-ray generator emitting an X-ray beam with a narrow width covering the width of the small width X-ray sensor 311, and adjusting a radiation direction of the X-ray generator in association with a positional movement of the small width X-ray sensor 311 so as to emit a focused X-ray beam. Various other configurations are possible.

Meanwhile, the X-ray image radiographing apparatus according to the embodiment described above may further include the controller 60 connected to the generating unit 32 and the sensing unit 31, and controlling the generating unit 32 to emit an X-ray beam XC focused in association with a positional movement of the small width X-ray sensor 311. In detail, the controller 60 may be, for example, connected to the small width X-ray sensor driver 312 and control the motor 315, and control a direction of the X-ray beam emitted from the generating unit 32 by using a control signal of the small width X-ray sensor driver 312 or a feed-backed signal including positional information of the small width X-ray sensor 311. Controlling the direction of the X-ray beam may be performed by controlling the motor 324 that drives the collimator 322 as described in the embodiment of the present figure. However, when the generating unit 32 is implemented in a different form as above, a detailed target that receives a control signal of the controller 60 may vary.

Figure 2:
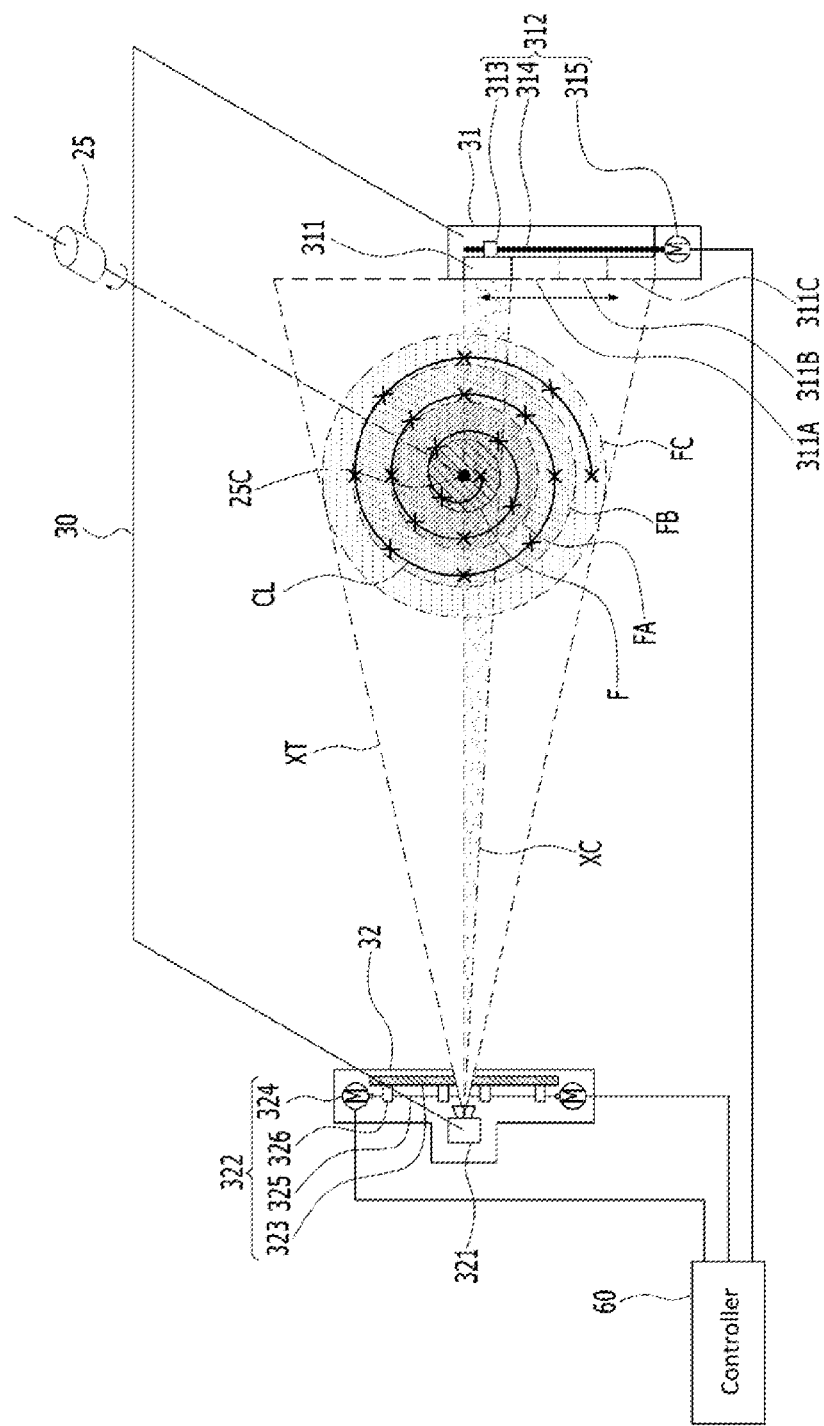
FIG. 2 is a view showing a movement trajectory of a virtual central point of an X-ray beam during a maximum FOV radiographing sequence of the X-ray CT radiographing apparatus according to an embodiment of the present invention.

FIG. 2 is a view showing a movement trajectory of a virtual central point of an X-ray beam during a maximum FOV radiographing sequence of the X-ray CT radiographing apparatus according to an embodiment of the present invention.

When radiographing a maximum FOV FC that may be implemented in the X-ray CT radiographing apparatus according to the present embodiment, the small width X-ray sensor 311 continuously moves outwardly or inwardly from the subject within the sensing unit 31. The generating unit 32 radiates an X-ray beam XC focused according to a position of the small width X-ray sensor 311. As a result, when connecting virtual centers of a path of the X-ray beam XC passing through the subject, a virtual center trajectory CL of the X-ray beam is shown in the figure. Herein, small x symbols are positions of the virtual centers of the X-ray beam at every 45 degrees with reference to a rotation angle of the rotation supporter 30.

The X-ray CT radiographing apparatus according to the present embodiment receives a FOV input which has various positions and shapes within a maximum FOV FC range before performing X-ray CT image radiographing, and the controller 60 operates the radiographing unit according to the input and performs an X-ray CT radiographing sequence. Motion of the radiographing unit constituting the X-ray radiographing sequence may be classified into two types.

The first type is a case where the selected input FOV has a concentric circular shape smaller than a maximum FOV, (for example, F, FA, FB). Herein, a movement trajectory of an X-ray beam may cover a part of a movement trajectory CL when radiographing the maximum FOV which is shown in the present figure. In detail, a shortened X-ray CT radiographing sequence may be configured so as to radiograph an X-ray transmitted image by moving a virtual center of the X-ray beam until the movement trajectory of the X-ray beam covers all of the input FOV having a concentric circular shape.

The second type is a case where the selected input FOV has a position and shape which are not related to a concentric circle of the maximum FOV. Herein, motion of the radiographing unit, that is, a rotation of the rotation supporter 30 by the rotation driver 225, and operation including a movement of the small width X-ray sensor 31 in the sensing unit 31 and an X-ray beam radiation direction in the generating unit 32, may be configured in a X-ray CT radiographing sequence which is identical to motion of radiographing the maximum FOV described above. Herein, a series of motions is performed by dividing a movement trajectory of an X-ray beam by a predetermined section unit, and the X-ray beam is temporarily turned OFF in a partial section where the movement trajectory passes a section out of the FOV, thus unnecessary X-ray radiation exposure may be eliminated. The above second type will be described below in more detail with reference to a figure.

Figure 3:
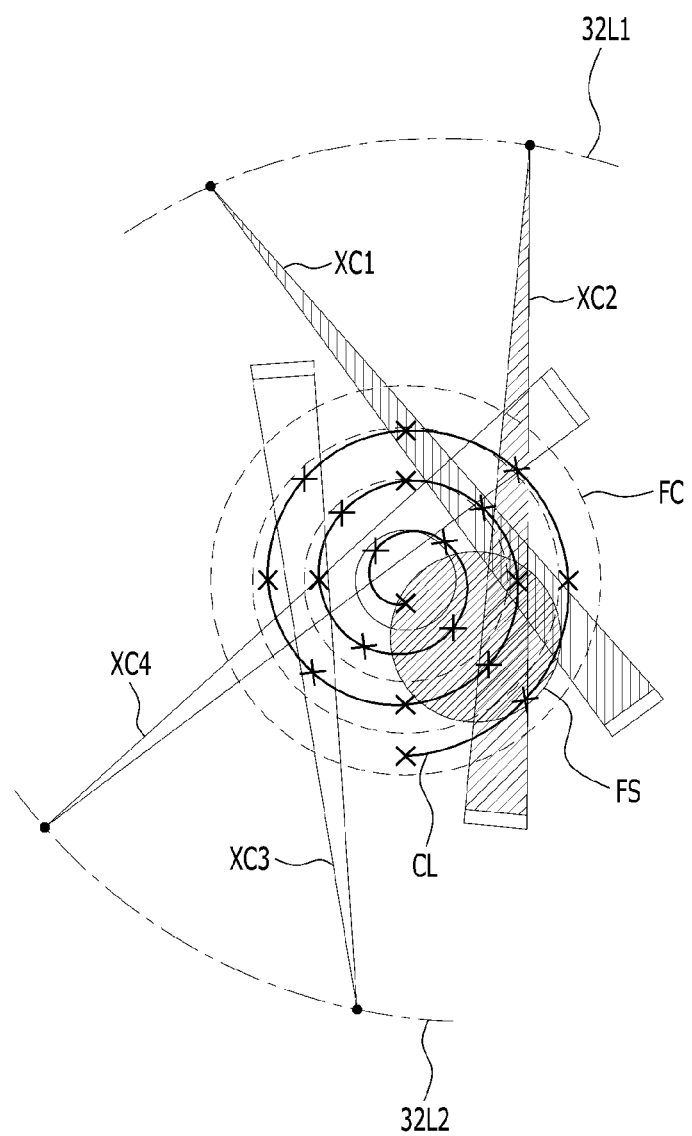
FIG. 3 is a view showing radiographing a partial FOV by using motion of a radiographing unit which is identical to a maximum FOV radiographing sequence in the X-ray CT radiographing apparatus according to an embodiment of the present invention.

FIG. 3 is a view showing radiographing a partial FOV by using motion of a radiographing unit which is identical to a maximum FOV radiographing sequence in the X-ray CT radiographing apparatus according to an embodiment of the present invention.

As shown in the figure, the selected input FOV FS may have a free position and shape in a range not exceeding the maximum FOV FC. Herein, a case for being selected a small circular FOV whose center is out of the center of the maximum FOV FC will be described as an example. The controller of the X-ray CT radiographing apparatus according to the present invention identically operates the radiographing unit when performing motion of radiographing the maximum FOV regardless of a size and shape of the selected input FOV FS. In the process, as shown in the figure, the movement trajectory of the X-ray beam passes various positions in various radiation directions, in a partial section 32L1 where the movement trajectory passes through at least part of the input FOV FS such as hatched portions XC1 and XC2, the X-ray beam is turned ON so that an X-ray transmitted image is obtained. When the movement trajectory of the X-ray beam passes through a section 32L2 which is not related to the input FOV FS as shown in the blank wedge-shaped portions XC3 and XC4, motion is performed while the X-ray beam is turned OFF so that unnecessary X-ray exposure may be prevented.

Figure 4:
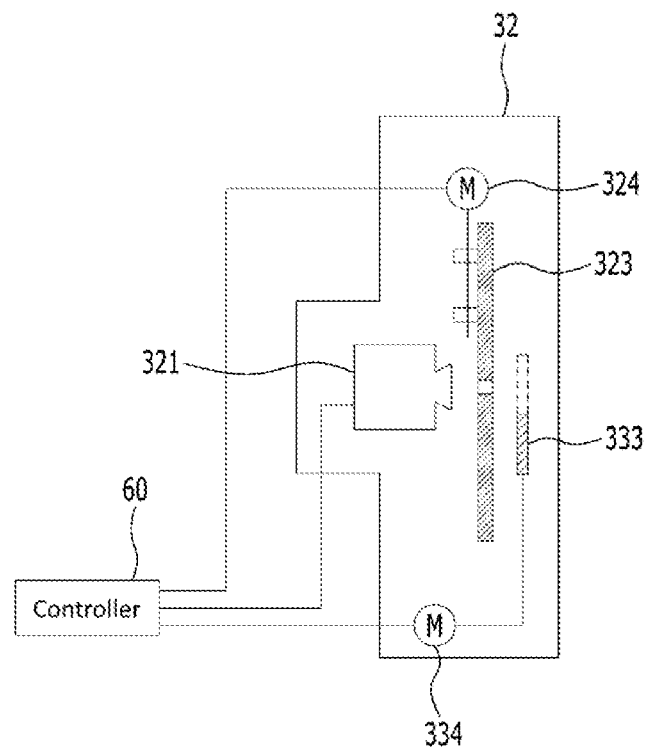
FIG. 4 is a view showing an X-ray generating unit of the X-ray CT radiographing apparatus according to an embodiment of the present invention.

FIG. 4 is a view showing an X-ray generating unit of the X-ray CT radiographing apparatus according to an embodiment of the present invention.

The present figure shows a configuration example of the generating unit 32 for tuning OFF an X-ray beam in a partial section when performing CT radiographing motion as described above. As an example, the controller 60 may be configured to adjust power or a control signal which is applied to the X-ray generator 321 so that the X-ray generator 321 temporally stops emitting X-rays. As another example, the controller 60 may include a blocking part that substantially blocks an X-ray beam generated in the generator 321 to be radiated on a FOV according to a signal, and the blocking part may be configured to include, for example, a shutter 333 for blocking an X-ray beam emitted from the X-ray generator 321 by operating an actuator 334. Meanwhile, as shown in FIGS. 1 and 2, when the collimator 322 includes at least two blades being separately operated, an X-ray beam may be temporally blocked by operating the blades.

Figure 5:
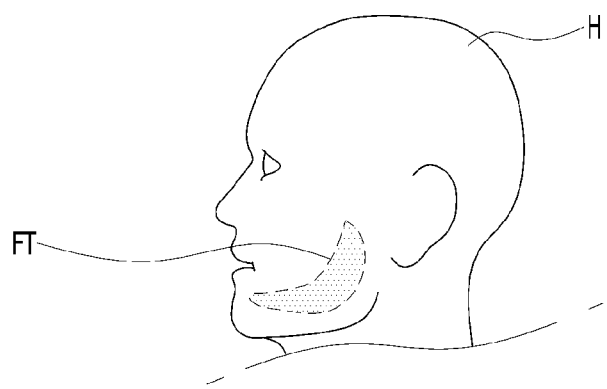
FIG. 5 is a view showing an example of a FOV that may be selected in the X-ray CT radiographing apparatus according to an embodiment of the present invention.

FIG. 5 is a view showing an example of a FOV that may be selected in the X-ray CT radiographing apparatus according to an embodiment of the present invention.

As shown in the figure, a shape of a FOV FT that may be selected is not limited to a cylindrical form. A free shape of a FOV may be input if the shape is represented by using an equation. The FOV may be input through an input device before performing X-ray CT radiographing, or may be input in a way that FOVs corresponding to a number of anatomical sites frequently used clinically are pre-stored and shown as examples, and a user selects one of them.

In addition, although it is not shown, the FOV that may be selected may be a plurality of areas. In other words, within the maximum FOV for radiographing, at least two FOV not overlapping each other may be selected to be radiographed.

Figure 6:
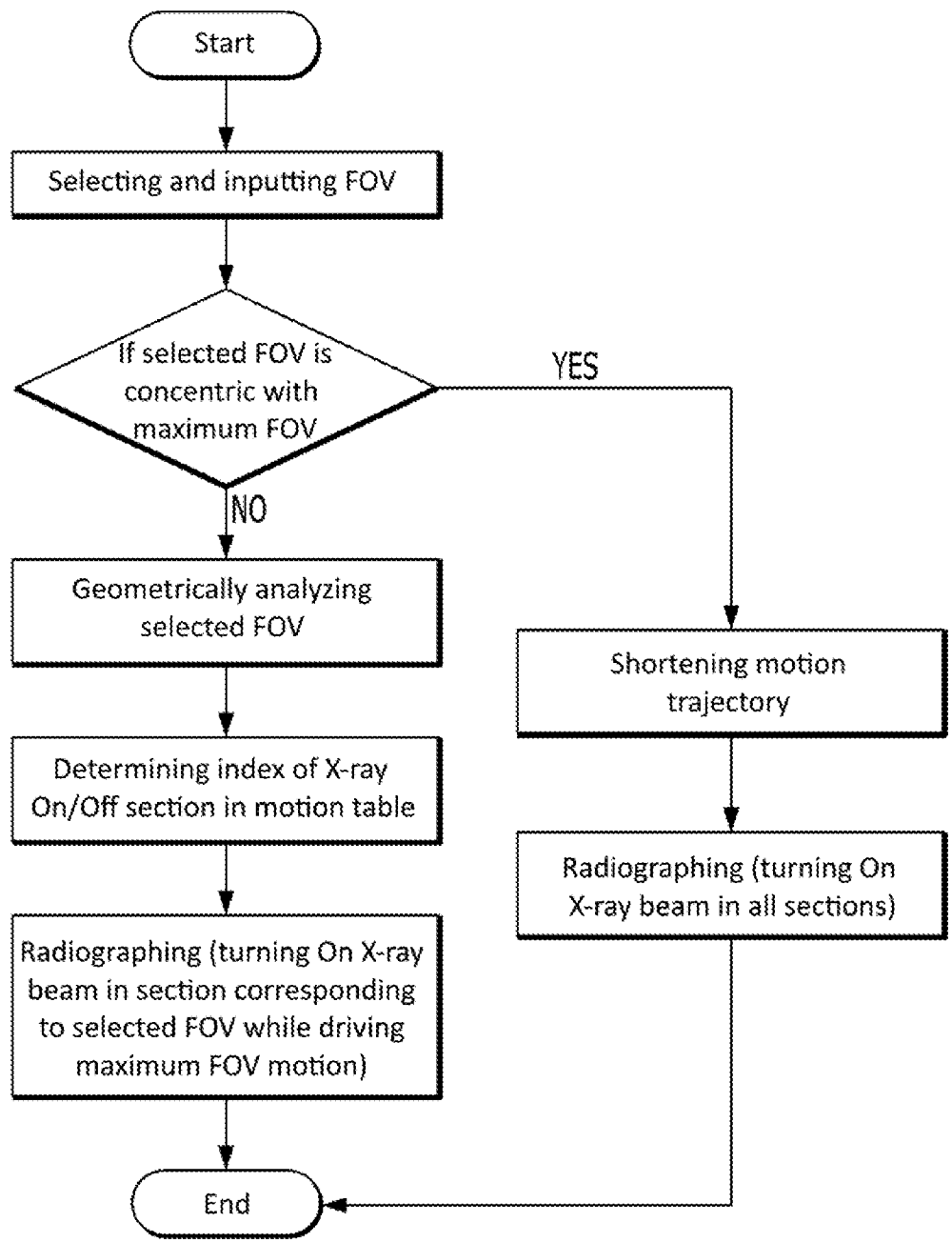
FIG. 6 is a view showing a method of radiographing an X-ray CT according to an embodiment of the present invention.

FIG. 6 is a view showing an X-ray CT radiographing method according to an embodiment of the present invention.

A method of radiographing an X-ray image by using the X-ray CT radiographing apparatus according to the present invention has been already described when describing the configuration of the X-ray CT radiographing apparatus and operation thereof, and a supplementary description is as follows. First, the X-ray CT radiographing method according to the present invention performs an X-ray CT radiographing sequence by using an X-ray CT radiographing apparatus including: a rotation supporter rotating based on one axis by a rotation driver, a generating unit including an X-ray generator and collimator disposed at one side of the rotation supporter to radiate an X-ray beam collimated in a predetermined width, and a sensing unit including a small width X-ray sensor disposed at a second side of the rotation supporter to face the generating unit with a subject in between and moving in a direction where the rotation supporter rotates.

First, a position and a shape of a FOV are input. An input method may be variously performed. As described above, a way of selecting any one of FOVs corresponding to a number of anatomical sites frequently used clinically may be used.

Then, a geometry form of the input FOV is analyzed in an equation, and, according to the result thereof, a section where an X-ray beam is turned ON and OFF is determined in a base motion table that is defined to be suitable for performing maximum FOV radiographing. Herein, the base motion table includes information in which motion of the radiographing unit for obtaining a CT image of the maximum FOV, that is, motion of the rotation driver, the generating unit, and the sensing unit is preset by sections. Herein, when one of pre-stored FOVs is selected, a process of analyzing the selected input FOV in an equation may be replaced with reading out information that is pre-stored by analyzing the same. As above, after determining the section where the X-ray beam is turned ON and OFF in the base motion table, according to the result thereof, an X-ray CT radiographing sequence is performed. When performing motion of the radiographing unit of the X-ray CT radiographing sequence, a method of turning ON and OFF the X-ray beam is as described above.

Meanwhile, before performing geometric analysis of the selected FOV after receiving the FOV from a radiographer, a process of determining whether the input FOV is a concentric circle smaller than the maximum FOV may be added. When it is determined that the input FOV is smaller than the maximum FOV, and has a shape of a concentric circle, a motion table shortened according to the same may be applied, otherwise, the input FOV does not have a shape of a concentric circle, a base motion table may be applied. When the shortened motion table is applied, motion may be performed while an X-ray beam is turned ON in the entire section.

Hereinafter, description will be made with reference to the example of the motion table described above.

TABLE 1

| Section index | Angle of rotation supporter ($\theta$) | Position of small width sensor |
|---|---|---|
| 1 | $\theta_1$ (=0 degrees) | $P_1$ |
| 2 | $\theta_2$ | $P_2$ |
| 3 | $\theta_3$ | $P_3$ |
| ... | ... | ... |
| 99 | $\theta_{99}$ | $P_{99}$ |
| 100 | $\theta_{100}$ (=1080 degrees) | $P_{100}$ |

First, Table 1 is an example of a base motion table. As shown in FIG. 2, an example of performing an X-ray CT radiographing sequence for a maximum FOV by moving the small width X-ray sensor continuously from one end to the other end within a range of about four times of a width thereof, and rotating the rotation supporter three times while focusing an X-ray beam in association with the small width X-ray sensor is shown. In addition, the Table 1 shows a movement trajectory of an X-ray beam of the radiographing sequence described above which is divided into 100 sections. However, the above is only one example.

TABLE 2

| Section index | Angle of rotation supporter ($\theta$) | Position of small width sensor | X-ray beam ON/OFF |
|---|---|---|---|
| 1 | $\theta_1$ (=0 degrees) | $P_1$ | ON |
| ... | ... | ... | ON |
| 5 | $\theta_5$ | $P_5$ | ON |
| 6 | $\theta_6$ | $P_6$ | OFF |
| ... | ... | ... | OFF |
| 10 | $\theta_{10}$ | $P_{10}$ | ON |
| ... | ... | ... | ON |
| 25 | $\theta_{25}$ | $P_{25}$ | OFF |
| ... | ... | ... | OFF |
| 100 | $\theta_{100}$ (=1080 degrees) | $P_{100}$ | OFF |

Table 2 shows an example where a section where an X-ray beam is turned ON and OFF is determined by sections by reflecting the result of geometric analysis of the selected FOV described above in the base motion table of Table 1 above. When the FOV is selected and input within the maximum FOV range, transmitted image frames required for reconstructing a CT image for the selected FOV is obtained as the radiographing unit of the X-ray CT radiographing apparatus performs motion as Table 1, and an X-ray beam is turned ON and OFF at several sections as described in Table 2.

TABLE 3

| Section index | Angle of rotation supporter ($\theta$) | Position of small width sensor |
|---|---|---|
| 1 | $\theta_1$ (=0 degrees) | $P_1$ |
| 2 | $\theta_2$ | $P_2$ |
| 3 | $\theta_3$ | $P_3$ |
| ... | ... | ... |
| 49 | $\theta_{49}$ | $P_{49}$ |
| 50 | $\theta_{50}$ (=540 degrees) | $P_{50}$ |

Table 3 shows an example of a shortened motion table. For example, when the radiographer selects a FOV corresponding to a concentric circle smaller than the maximum FOV FC in FIG. 2 and all transmitted image frames required for reconstructing a X-ray CT image are obtained by motion in which the rotation supporter rotates 540 degrees, radiographing is performed while an X-ray beam is only turned ON in sections corresponding to section indexes from 1 to 50.

Meanwhile, as above, performing motion or radiographing while an X-ray beam is turned ON means radiating an X-ray beam for obtaining an X-ray transmitted image frame corresponding to a desired section, but it is not limited that the X-ray beam continuously maintains an ON state.

INDUSTRIAL APPLICABILITY

The present invention relates to an X-ray CT radiographing apparatus and a radiographing method thereof, and may be used for a medical X-ray diagnosing apparatus, more particularly, may be used in the field of a dental X-ray diagnosing apparatus.

The invention claimed is:

1. An X-ray computer tomography (CT) radiographing apparatus, the apparatus comprising:
   a rotation supporter rotating by a rotation driver;
   a generating unit disposed in a first side of the rotation supporter, and including an X-ray generator emitting X-rays and a collimator to radiate a collimated X-ray beam;
   a sensing unit disposed in a second side of the rotation supporter to face the generating unit with a field of view (FOV in between, and including a X ray sensor and a motor for moving the X-ray sensor in a tangential direction of a rotation trajectory when the rotation supporter rotates; and
   a controller blocking the X-rays or stopping emission of the X-rays radiated toward the FOV in predetermined sections of the rotation trajectory while the rotation supporter is rotating for performing X-ray radiographing,
   wherein a width w2 of the X-ray sensor is narrower than (m×(w1/2)), where m is a magnification ratio and w1 is a maximum width of FOV.

2. The apparatus of claim 1, wherein the controller stops the emission of the X-rays from the X-ray generator for the predetermined sections.

3. The apparatus of claim 1, wherein the controller physically blocks the X-rays emitted from the X-ray generator in the predetermined sections of the rotation trajectory by using the collimator.

4. The apparatus of claim 1, wherein the generating unit further includes a shutter physically blocking the X-ray beam emitted from the X-ray generator in the predetermined sections of the rotation trajectory.

5. The apparatus of claim 1, further comprising an image reconstructing unit providing a three-dimensional X-ray image for at least one part within the FOV by reconstructing a result detected by the X-ray sensor.

6. An X-ray computer tomography (CT) radiographing method, the method comprising:
  receiving an input of a position and a shape of a field of view (FOV); and
  performing X-ray radiographing for the FOV by rotating a generating unit including an X-ray generator and, in association thereof, simultaneously rotating a sensing unit including a motor and an X-ray sensor with the FOV in between, the motor moving the X-ray sensor in a tangential direction of the rotation trajectory, and blocking X-rays or stopping emission of the X-rays emitted from the X-ray generator toward the FOV in predetermined sections of the rotation trajectory according to the position and the shape of the FOV while rotating the generating unit and the sensing unit for performing X-ray radiographing,
  wherein a width w2 of the X-ray sensor is narrower than (m×(w1/2)), where m is a magnification ratio and w1 is a maximum width of FOV.

7. The method of claim 6, wherein in the X-ray radiographing, the emission of the X-rays is stopped by controlling the X-ray generator to be turned ON/OFF or the X-rays is blocked by physically blocking an X-ray beam radiated toward the FOV.

8. The method of claim 6, further comprising, after the X-ray radiographing, providing a three-dimensional X-ray image for at least one part within the FOV by reconstructing a result detected by the X-ray sensor.

* * * * *